US011829523B2

(12) United States Patent
Drozdov et al.

(10) Patent No.: US 11,829,523 B2
(45) Date of Patent: *Nov. 28, 2023

(54) SYSTEMS AND METHODS FOR ANATOMY-CONSTRAINED GAZE ESTIMATION

(71) Applicant: BLINK TECHNOLOGIES INC., Palo Alto, CA (US)

(72) Inventors: Gilad Drozdov, Haifa (IL); Oren Haimovitch-Yogev, Los Altos, CA (US); Uri Wollner, Ramat Gan (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/971,600

(22) Filed: Oct. 23, 2022

(65) Prior Publication Data
US 2023/0074569 A1 Mar. 9, 2023

Related U.S. Application Data

(63) Continuation of application No. 17/298,935, filed as application No. PCT/IL2019/051306 on Nov. 28, 2019, now Pat. No. 11,513,593.

(60) Provisional application No. 62/772,657, filed on Nov. 29, 2018.

(51) Int. Cl.
G06F 3/01 (2006.01)
G06T 7/73 (2017.01)
G06V 40/16 (2022.01)
G06V 40/18 (2022.01)
G06T 1/20 (2006.01)
G06T 7/00 (2017.01)
A61B 3/113 (2006.01)
G06V 10/764 (2022.01)
G06V 10/82 (2022.01)
G06V 10/44 (2022.01)
G06V 10/20 (2022.01)

(52) U.S. Cl.
CPC .............. *G06F 3/012* (2013.01); *A61B 3/113* (2013.01); *G06F 3/013* (2013.01); *G06T 1/20* (2013.01); *G06T 7/0012* (2013.01); *G06T 7/73* (2017.01); *G06V 10/255* (2022.01); *G06V 10/44* (2022.01); *G06V 10/764* (2022.01); *G06V 10/82* (2022.01); *G06V 40/161* (2022.01); *G06V 40/171* (2022.01); *G06V 40/18* (2022.01); *G06V 40/193* (2022.01); *G06T 2207/20084* (2013.01); *G06T 2207/30041* (2013.01)

(58) Field of Classification Search
CPC ....... A61B 3/113; A61B 3/0025; A61B 3/111; A61B 3/112; A61B 3/14; G06F 3/012; G06F 3/013; G06T 1/20; G06T 7/0012; G06T 7/73; G06T 2207/20084; G06T 2207/30041; G06V 10/255; G06V 10/44; G06V 10/764; G06V 10/82; G06V 40/161; G06V 40/171; G06V 40/18; G06V 40/193
See application file for complete search history.

(56) References Cited

U.S. PATENT DOCUMENTS

| 2015/0293588 | A1* | 10/2015 | Strupczewski | ......... G06F 3/012 382/117 |
| 2018/0081434 | A1* | 3/2018 | Siddiqui | ................ G06V 40/20 |
| 2020/0004326 | A1* | 1/2020 | Sipolins | ................ G06T 19/006 |

* cited by examiner

Primary Examiner — Premal R Patel
(74) Attorney, Agent, or Firm — ALPHAPATENT ASSOCIATES, LTD; Daniel J. Swirsky

(57) ABSTRACT

Anatomically-constrained gaze estimation providing a point of reference (PoR) in a 3D field and/or 2D plane, based on 6 DOF head pose constrained by the eyeball center being fixed in a common 3D coordinate system.

20 Claims, 8 Drawing Sheets

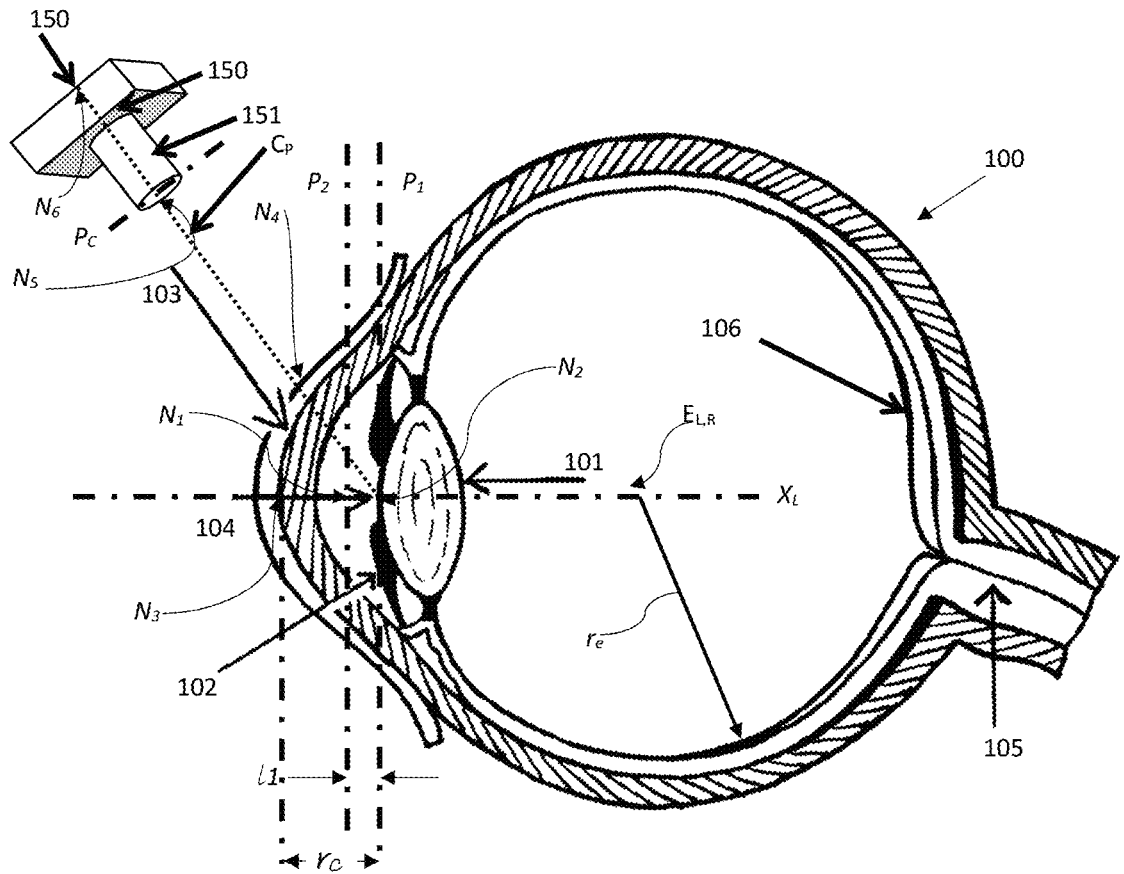
FIG. 1A
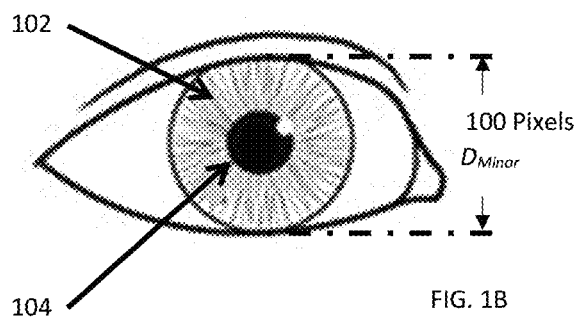
FIG. 1B
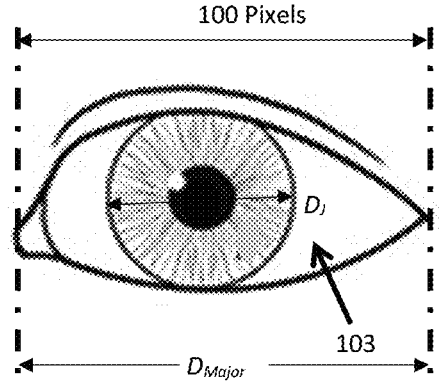

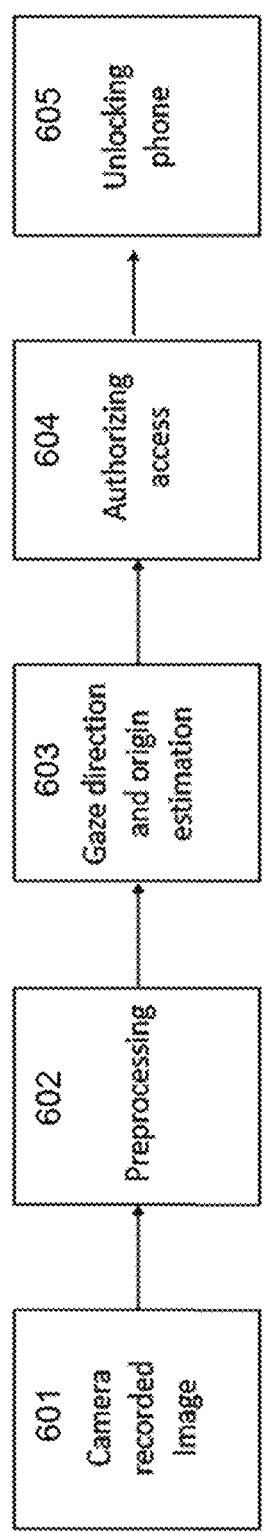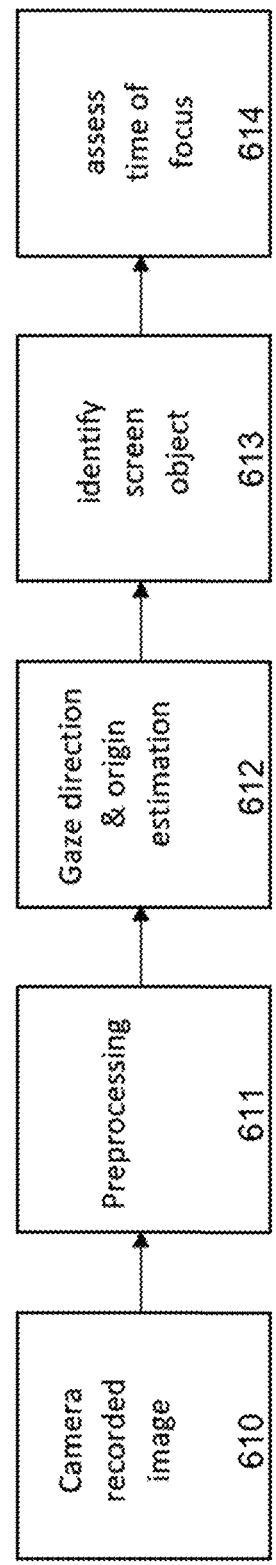

SYSTEMS AND METHODS FOR ANATOMY-CONSTRAINED GAZE ESTIMATION

COPYRIGHT NOTICE

A portion of the disclosure herein below contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND

The disclosure is directed to systems, methods and programs for providing anatomically-constrained gaze estimation. More specifically, the disclosure is directed to systems, methods and programs for providing anatomically-constrained point of reference (PoR) in a 3D space and/or 2D plane, based on constrained oculometry.

Estimation of a person's point-of-gaze (also referred to as point-of-regard) has become an important tool in a variety of applications, including, for example, the study of visual and oculomotor systems, the study of reading behavior, marketing/advertising research, and the control of device user interfaces (e.g., graphical user interfaces) using eye movements.

Additional applications for systems, methods and processor-readable media for gaze estimation have many potential applications in the medical, scientific, engineering, manufacturing, military, and entertainment domains. Example applications can be, for example as a tool for the medical diagnosis of ocular functions, as an aid to the paraplegic handicapped, for the measurement of ocular functions and workload in human factors studies, as a measure of subject training, as a tool for fatigue monitoring, as part of an electronic safety net to detect performance degradation due to pilot/driver incapacitation in driven, piloted and tele-operated vehicles, as a component of an electronic intelligent pilot-vehicle interface used for adaptive aiding in piloted and tele-operated vehicles, for task scan analysis including measuring situation awareness, for human operator control of machines and interaction with computer games, and for advertisement placement determination and usability analysis. The systems, methods and processor-readable media may be designed for use with head-mounted video displays such as those that have been developed for virtual reality, stereographic displays, monocular or binocular vision helmet-mounted displays, and night vision goggles. These displays can be used, for example, in piloted helicopters, vehicles, and control stations for teleoperated robotics such as remote operated surgery and the like.

An example for eye-tracking is videooculography based upon the optical measurement of reflected light from the human eye, commonly near-infrared (NIR) light for an image of the eye region, and it's corresponding refraction from the cornea. In its simplest form, an oculometer contains a single infrared light source which is directed at the eye and the reflected light is imaged onto a charge-injection (CID) or charge-coupled device (CCD) sensor array. The image of the eye is then electronically processed to determine the corneal reflection, the pupil centroid orientation, or both. These parameters are used to determine the angular location of the eye relative to the camera within a fair degree of accuracy. The technology is either head-mounted or mounted in a panel in front of the user. Furthermore, the technology is most accurate for a front camera view of the eye; however, the accuracy decreases with offset because much of the present technology is based on pupil (or glint, or in other words, corneal reflection detection) image processing using simple perspective computations. However, a problem is the image distortion caused by corneal surface refraction and built in distortion of the CID/CCD/CMOS optic sensors. The accuracy decreases with side-view because of the non-uniform distortions in the pupil and Iris image caused by the corneal surface refraction with pupil offset, and localization of the Iris. This non-linearity in distortion causes the centroid computed for the image ellipsoid to be displaced from the centroid for the true image resulting in computational error.

Furthermore, the technology estimates only the principal visual-axis and does not account for the effect on sight direction of the torsional roll of the eye with accompanying vertical vergence eye movement that is induced during the tilting of the head a common occurrence during target tracking and user motion, and does not account for the individual non-symmetry. Moreover, those existing methods of estimating point-of-gaze that do take into account the angular offset between optical and visual axes are intolerant to substantial rotations of a person's head relative to an estimation device, or substantial rotations of the estimation device relative to the head, and thus fail to provide accurate estimates of point-of-gaze when such head/device rotations occur.

These and other shortcomings of the existing technology are sought to be resolved herein.

SUMMARY

Disclosed, in various implementations, examples and embodiments are systems, methods and programs for providing a point of reference (PoR) in a 3D space and/or 2D plane, based on user-personalized constrained oculometry (identified for each eye).

In an implementation, provided herein is a system for providing a user-specific gaze estimation, the system comprising: an imaging module comprising an optic sensor directed to the user; a display; a graphic processing module (GPM); a central processing module (CPM), in communication with the imaging module, the display, the GPM and a memory having thereon a processor-readable media with set of executable instructions configured, when executed to cause the CPM to: using the imaging module, capture an image of the user's face; extract a plurality of features from the captured image; using the plurality of extracted features, determine the user's head pose (within its six-degrees of freedom (DOF)) in a predetermined Cartesian coordinate system; unproject the user's pupil and Iris of both eyes from a portion of the plurality of extracted features, into the predetermined Cartesian coordinate system, forming a right eye and a left eye unprojected, three dimensional (3D) contours; and using the right and left eyes' unprojected, three dimensional (3D) contours, determine at least one of eye location, gaze direction, and point of regard (PoR), wherein the eyeball center is fixed in the Cartesian coordinates, thus providing anatomically constrained (in other words, the eyeball center in 3D space coordinates) gaze estimation.

In another implementation, provided herein is a method of providing at least one of an anatomically constrained, user specific: eye location, gaze direction, and PoR, implementable in a system comprising an imaging module comprising an optic sensor directed to the user, a display, a graphic processing module (GPM), a central processing module (CPM), wherein the CPM is in communication with the imaging module, the display, the GPM and a memory having thereon a processor-readable media with set of executable instructions, the method comprising: using the imaging module, capturing an image of the user's face; extracting a plurality of features from the captured image; using the plurality of extracted features, establishing the user's head pose in a predetermined Cartesian coordinate system; unprojecting the user's pupil and Iris of both eyes from a portion of the plurality of extracted features, into the predetermined Cartesian coordinate system, forming a right eye and a left eye unprojected, three dimensional (3D) contours; and using the right and left eyes' unprojected, three dimensional (3D) contours, determining at least one of eye location, gaze direction, and point of regard (PoR), wherein the eyeball center is fixed in the Cartesian coordinates, thus providing anatomical constrains.

In yet another implementation, provided herein is a computer program product for providing at least one of a user specific: eye location, gaze direction, and PoR, implementable in a system comprising an imaging module with an optic sensor directed to a user, a display, a graphic processing module (GPM), and a central processing module (CPM), wherein the CPM is in communication with the imaging module, the display, the GPM and a memory having thereon the processor-readable media, comprising a set of executable instructions configured when executed, to cause the CPM to: using the imaging module, capture an image of the user's face; extract a plurality of features from the captured image; using the plurality of extracted features, establishing the user's head pose in a predetermined Cartesian coordinate system; unproject the user's pupil and Iris of both eyes from a portion of the plurality of extracted features, into the predetermined Cartesian coordinate system, forming a right eye and a left eye unprojected, three dimensional (3D) contours; and using the right and left eyes' unprojected, three dimensional (3D) contours, determine at least one of eye location, gaze direction, and point of regard (PoR), wherein the eyeball center is fixed in the Cartesian coordinates, thus providing anatomical constrains.

These and other features of the systems, methods and programs for providing an anatomically constrained, point of reference (PoR) in a 3D field and/or 2D plane, will become apparent from the following detailed description when read in conjunction with the figures and examples, which are exemplary, not limiting.

BRIEF DESCRIPTION OF THE FIGURES

For a better understanding of systems, methods and programs for providing a point of reference (PoR) in a 3D field and/or 2D plane, with regard to the implementations thereof, reference is made to the accompanying examples and figures, in which:

FIG. 1A, illustrates a cross section of a human eye with front view of human eyes illustrated in FIG. 1B;

FIGS. 6A-6B, illustrate flow charts of various applications;

DETAILED DESCRIPTION

Provided herein are implementations of systems, methods and programs for providing a point of reference (PoR) in a 3D field and/or 2D plane, based on anatomically constrained oculometry.

In an implementation, the systems, methods and programs for providing a point of reference (PoR) in a 3D field and/or 2D plane, based on user specific, personalized and anatomically constrained oculometry can be comprised of a standard optical sensor (in other words, imaging module) and a screen or display, configured to predicts the gaze direction of a user or (predict and determine) the user's point of regard (PoR) on the screen. In other words, the systems, methods and programs for providing a point of reference (PoR) in a 3D field and/or 2D plane, based on user specific, personalized constrained oculometry can be configured to simultaneously tracking of both eyes allowing the measurement of the optical convergence point in the either real, or virtual three dimensional (3D) workspace and thus, the PoR.

Figure 2A:
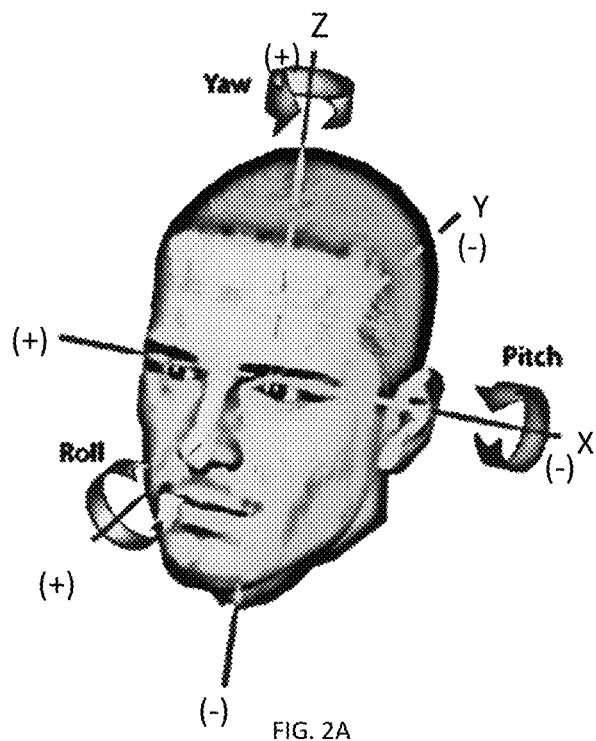
FIG. 2A, illustrates the conventional axes providing six degrees of freedom in describing the head position in 3D space, with angular orientation schematic illustrated in FIG. 2B.
Figure 2B:
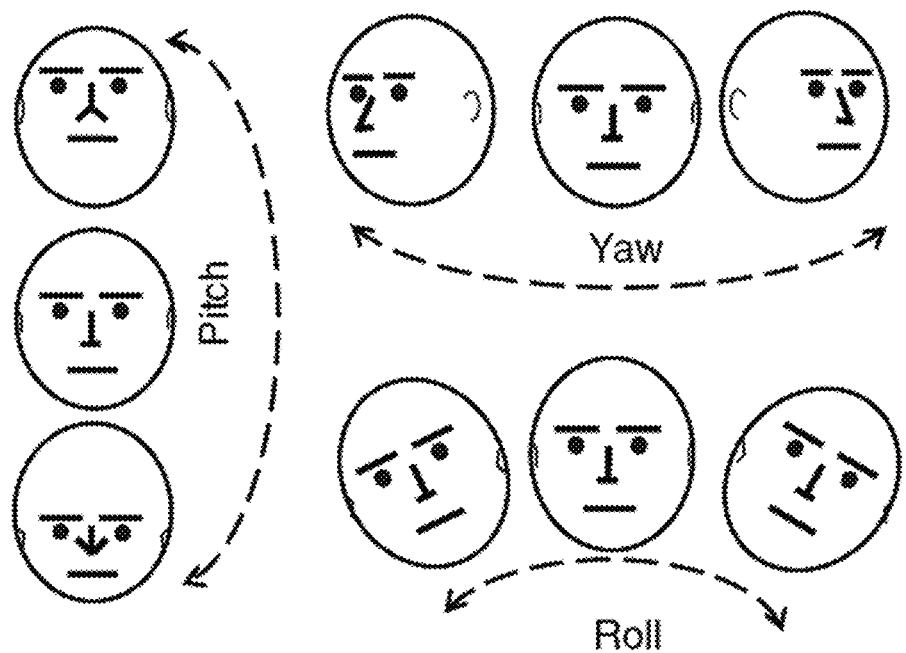

This is achieved, partly, through deep-learning-based, landmark detection of iris and pupil contours on recorded images obtained by the imaging module comprising an optical sensor that is directed toward the user, as well as deep-learning-based algorithm for estimating user's head pose (see e.g., FIGS. 2A-2B) with six (6) degrees of freedom (DOF), namely localization in 3D space (x,y,z) and angular positioning (pitch, yaw, roll)). Additionally, geometrical and ray tracing methods can be employed to unproject the iris and pupil contours from the optic sensors in the imaging module's plane onto 3D space, thus, allowing to estimate the personalized, user-specific eye (used interchangeably with "eyeball") location (based on an initial geometry eyeball-face model, that relates between visible feature such as facial-landmarks to non-visible features such as eyeball center, refraction index, corneal-eyeball deviation etc.) and gaze direction in the imaging module's space (e.g., Cartesian) coordinate system (in other words, a system of representing points in a space of given dimensions by coordinates). Likewise, the term "Cartesian coordinate system" denotes a system where each point in a 3D space may be identified by a trio of x, y, and z coordinates. These x, y and z coordinates are the distances to a fixed X, Y and Z axes. In the context of the implementations disclosed, the 3D coordinate system refers to both the 3D position (x,y,z) and 3D orientation (pitch, roll, yaw) of the model coordinate system relative to the camera coordinate system.

The components used for the operation of the system can be, for example an imaging module with a single optical (e.g., passive) sensor having known distortion and intrinsic properties, obtained for example, through a process of calibration. These distortion and intrinsic properties are, for example, modulation-transfer function (MTF), focal-length for both axes, pixel-size and pixel fill factor (fraction of the optic sensor's pixel area that collects light that can be converted to current), lens distortion (e.g., pincushion distortion, barrel distortion), sensor distortion (e.g., pixel-to-pixel on the chip), anisotropic modulation transfer functions, space-variant impulse response(s) due to discrete sensor elements and insufficient optical low-pass filtering, horizontal line jitter and scaling factors due to mismatch of sensor-shift- and analog-to-digital-conversion-clock (e.g., digitizer sampling), noise, and their combination. In an exemplary implementation, determining these distortion and intrinsic properties is used to establish an accurate sensor model, which can be used for calibration algorithm to be implemented.

The systems for implementing the methods provided, using the programs disclosed further comprise a computing device for analyzing the image recorded by the optical sensor according to the algorithms used. Moreover, as part of the analysis of the recorded image, the left or right eye region of the user—shown in FIG. 1B, can be defined as the region encompassing the corners of the eye as well as the upper and lower eyelids—having a minimal size of 100×100 pixels, in other words, each of the left, and right eyes' region comprises a quadrilateral polygon (e.g., a rectangle) of at least 100 pixel by 100 pixel extending between the corners of each eye as well as between the upper and lower eyelids, when the eye is open.

Accordingly and in another exemplary implementation, provided herein is a system for providing a user-specific gaze estimation, the system comprising: an imaging module comprising an optic sensor directed to the user; a display; a graphic processing module (GPM), comprising at least one optical sensor; a central processing module (CPM), in communication with the imaging module, the display, the GPM and a memory having thereon a processor-readable media with set of executable instructions configured, when executed to cause the CPM to: using the imaging module, capture an image of the user's face; extract a plurality of features from the captured image; using the plurality of extracted features, determine the user's head pose in a predetermined Cartesian coordinate system; unproject the user's pupil and Limbus of both eyes from a portion of the plurality of extracted features, into the predetermined Cartesian coordinate system, forming a right eye and a left eye unprojected, three dimensional (3D) contours; and using the right and left eyes' unprojected, three dimensional (3D) contours, determine at least one of eye location, gaze direction, and point of regard (PoR).

Figure 3:
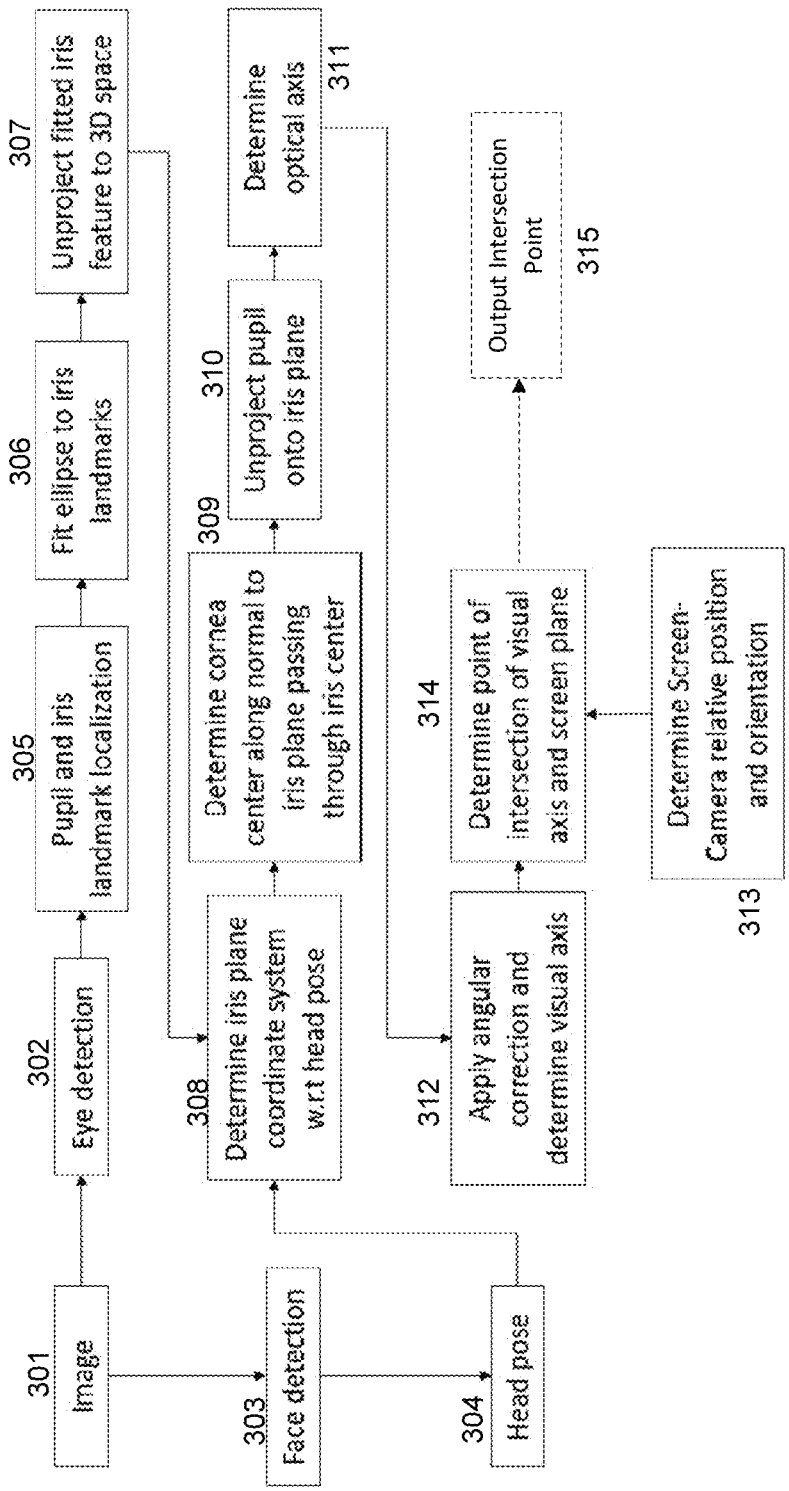
FIG. 3, is a schematic illustrating an implementation of a flow chart for determining PoR.

An example of implementing the methods described using the systems provided, is illustrated in FIG. 3.

To build an accurate eye model, the locations of the iris of both eyes is established in a 3D coordinate system in which the eyeball center ($E_{L,R}$, FIG. 1) is fixed. The head pose coordinate system can serve as the basis for establishing the iris location. In an example, an eye-face model—the location of both eyeball centers is determined in head coordinates (with regard to facial landmarks). An example of a pseudo code for the algorithm of the eye-model building (See e.g., FIG. 3), can be as follows:

Eye Face model building Example:

Input:
$\{F\}_{i=1...N}$ - N Image Frames
C - Camera's intrinsics, projection matrix and distortion coefficients
K - Camera Matrix Eye Face model building Example:

Output -
$E_L$, $E_R$ - Left and Right Eyball centers
$\overline{IE}_L$, $\overline{IE}_R$- iris - Eye center offsets
Algorithm:
1. For each Frame, $F_i$:
   a. $\widetilde{F}_i \leftarrow$ IntrinsicDistortionCorrection($F_i$, C)
      Was done by multiplying with a camera projection matrix in order to bring the data to a similar form to what the network knows how to handle.
   b. $\{LP\}_{j,eye}$, $R_H$, $T_H$,Lanmarks$_i$ $\leftarrow$ HeadposeLandmarkIrisDetection($\widetilde{F}_i$)
      (See e.g., FIG. 3, 302,303,304,305)
      Was done by deep neural networks. $R_H$, $T_H$ denote head rotation and translation respectively.
   c. For each eye:
      i. ProjectedIrisEllipse($\alpha$, b, $\phi$, $x_C$, $y_C$ $\leftarrow$ Ellipse Fitting($\{LP\}_{j,eye}$) (306)

The iris was estimated as a circle mapped to an ellipse by the camera's projection:
   ii. IrisCone$_{CCS}$$\leftarrow$Unproject(ProjectedIrisEllipse, K) (307a)—Produces a cone in Camera's Coordinate System which is the result of multiplying the projected ellipse points with the inverse of the camera projection matrix (each point is mapped to a line in 3D).
   iii. IrisCone$_{HCS}$$\leftarrow$ApplyRotationTranslation($R_H$, $T_H$, IrisCone$_{CCS}$) (307b)

This stage was done to bring the cone (and by extension the Iris circle) to a coordinate system in which the eyeball center is fixed $\{$3DIrisCircle$_{HCS}\}_{+,-}\leftarrow$CircularConeIntersection (IrisCone$_{HCS}$,$r_I$) (307c)

As specified in the step (i) hereinabove; the Iris circle was brought to a coordinate system in which the eyeball center was fixed, which was done assuming that the iris is a circle positioned on the surface of the eyeball sphere (which projection results in the ellipse detected by the camera). Thus the circular intersections with the cone, were its' possible locations; and using $r_I$=6 mm—population mean (of iris' dimensions) resulted in 2 possible iris circles—denoted +,−. The Iris(Circle) rotation angles were then denoted $\eta,\xi$
2.      $\{E, r_{eye}\}_{EyE\in L,R}$, $\mathcal{R}_i\leftarrow$Swirsky($\{\{$3DIrisCircle$_{HCS}\}_{+,-}\}_{i=1}^N$)

An initial guess for eyeball centers and Radii was achieved using the algorithm specified in [2]—for each eye the Iris circles was found, which normal vector intersect in a single point, and that point. The eyes' rotations ($\mathcal{R}_i$) was also obtained—which are the Iris circle normal in head coordinate system $$E_L, E_R, \overline{IE}_L, \overline{IE}_R, d_{L,R} = \qquad\qquad 3$$

$$\operatorname{argmin}_{E_L,E_R,\overline{IE}_L,\overline{IE}_R,d(E_L,E_R)} \sum_{\{k\in L,R\}} \sum_{i=1}^{N} \left|\sum_{j=1}^{M} dist\bigl(LP_{i,j,k} - \wp(\mathcal{R}_{i,k}(EM_k))\bigr)\right|_2$$

s.t. $d_{L,R}$ = constant.

In this step, the (rotated) eye model was obtained from the head coordinate system and the projection operator $\wp$ was computed by first applying rotation and translation with $R_H^{-1}$, $-T_H$ followed by multiplication with the camera projection matrix K of the 3D eye, while $R_i$ was the established eye rotation in every frame $F_i$—also applied using matrix multiplication of the simplified 3D eye model (a sphere of radius $r_{eye}$, with limbus in radius IE centered at $E_{R,L}$, See e.g., FIG. 1). These parameters defined the (hidden from camera) eyeball center positions with regard to head-pose, and thus mapping to the facial landmarks which allowed the inference of the eyeball center from the camera-detected visible landmarks.

The process was repeated for both eyes resulting in $E_L$, $E_R$, $IE_L$, $IE_R$ leading to a personalized parameter of the locations of both eyes as related to each other, constrained anatomically by the eyeball centers.

Prior to implementing the methods using the systems provided, the user initially performs an intrinsic calibration step (see e.g., FIG. 8), during which, the user's eyes' 100, 100' movement pattern is analyzed while looking at pre-defined reference points $801_i$ on display 800. In other words, the CPM will render a point of reference $801_i$ on display 800 with surface 802 and the user will focus on these reference points ($801_i$), whereby vision lines from the left ($VL_L$) and right ($VL_R$) eyes 100, 100' respectively, are determined following image capture- and their point of convergence $803_j$ is mapped to the originally rendered points of reference $801_i$. In the calibration stage, the extrinsic calibration further comprises determining the relative position and orientation of the display with respect to the optic sensor.

Figure 8:
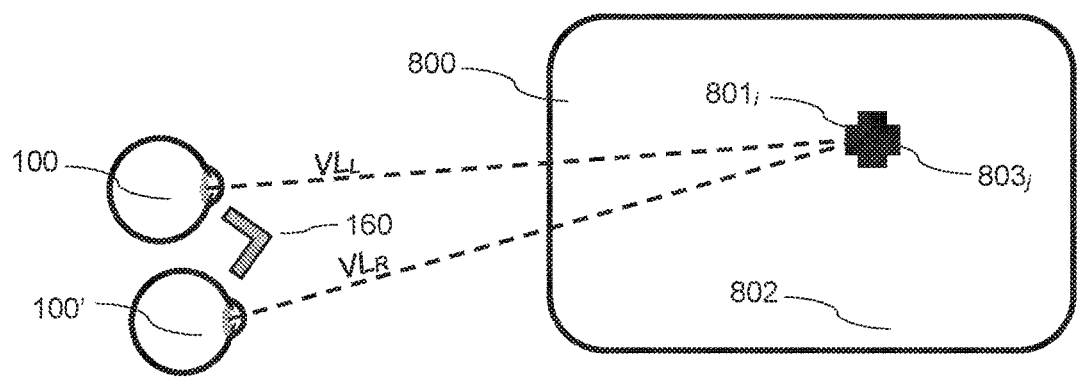
FIG. 8, illustrates an implementation of calibration and/or display and/or measurement used.

Turning now to FIGS. 1A-3, where, as described herein-above with reference to FIG. 8, a plurality of images of the user interactions with the screen in identifying and focusing on points of reference 801$i$ are captured 301, after which, two separate algorithms for eye region localization/detection 302 and face detection 303 are employed.

For example, the algorithm used for eye region localization can comprise assigning a vector to every pixel in the edge map of the eye area (see e.g., FIG. 1B), which points to the closest edge pixel. The length and the slope information of these vectors can consequently be used to detect and localize the eyes by matching them with a training set (obtained ion the intrinsic calibration phase). Additionally, or alternatively, a multistage approach is used for example to detect facial features (among them are the eye centers, or pupils 104) using a face detector, with pairwise reinforcement of feature responses, and a final refinement by using an active appearance model (AAM). Other methods of eye region localization can be employed, for example: using edge projection (GPF) and support vector machines (SVMs) to classify estimates of eye centers using an enhanced version of Reisfeld's generalized symmetry transform for the task of eye location, using Gabor filters, use feature triplets to generate face hypothesis, register them for affine transformations, and verify the remaining configurations using two SVM classifiers, and using an eye detector to validate the presence of a face and to initialize an eye locator, which, in turn, refines the position of the eye using the SVM on optimally selected Haar wavelet coefficients. These methods can be used either alone or in combination with the face detection algorithm.

The face detection algorithm is further used to compute head pose in six degrees of freedom (DOF). Some exemplary methods for estimating head pose localization and angular orientation can be a detector array method (DAM), in which a series of head detectors are trained, each configured to classify a specific pose and assign a discrete pose to the detector with the greatest support, a technique using machine learning and neural networks. This method can be supplanted or replaced by Nonlinear Regression Methods (NRM), which estimates head pose by learning a nonlinear functional mapping from the image space to one or more pose directions, normally using regression tools and neural networks. Additional methods can be, for example: a flexible algorithm, in which a non-rigid model is fit to the facial structure of the user in the image and wherein head pose is estimated from feature-level comparisons or from the instantiation (exemplifying e.g.,) of the parameters, using the location of extracted features such as the eyes, mouth, and nose tip 160 (see e.g., FIG. 8) to determine pose from their relative configuration (see e.g., FIG. 2B), recovering the global pose change of the head from the observed movement between video frames then using weighted least squares on particle filtering to discern the head pose. In an exemplary implementation, the head pose determination 304 method used, can be a hybrid method, combining one or more of the aforementioned methods to overcome the limitations inherent in any single approach. For example, using local feature configuration (eyes, nose tip, lips e.g.,) and sum of square differences (SSD) tracking, or principal component analysis comparison and continuous density hidden Markov Modeling (HMM). The existing models are additionally extended to include, for example eyeball landmarks, both visible (e.g. Pupil-center, Pupil contour and limbus contour) as well as non-visible (e.g. eyeball center, iris-corneal offset, cornea major axis). These are determined through a calibration process between the visible facial-eye landmarks (or feature) to the non-visible face-eye landmarks (or features) through a process of fixation, or focusing, by a subject on a known target presented to the subject. The final outcome of this procedure, is a personalized face-eye model (which is configured per-user) that best estimates the location of the visibly and non-visible landmarks (or features) in the sense of Gaze-reprojection (matrix)-error (GRE).

As indicated, using eyes' feature(s), or landmarks extraction, the Limbus 102 (see e.g., FIG. 1) and pupil 104 are localized and Limbus 102 is mapped 306 to an ellipsoid, after which the fitted (mapped) ellipsoid is unprojected 307 from the camera 2D plane into the 3D space volume, in which the user-specific eye surface is defined. In an exemplary implementation, each data point defines a viewing ray from the observer's eyes 100, to the viewing area 802. The unprojection process of step 307 computes the interception of such a viewing ray with the surface of the eye 100 defined in the three-dimensional space. This can be accomplished by multiplying the x, y coordinates of each data point with an unprojection matrix, resulting in the x, y, z coordinates of a corresponding point on the three-dimensional surface of the eye 100, as constrained 308 by the angular parameters of the head pose (pitch, yaw and roll), determined in step 304. For example, the unprojection matrix may be calculated as an inverse of the projection matrix used for rendering the three-dimensional surface of the eye 100 on the two-dimensional image plane (screen 802) of the display device 800. It is further noted that the Open Graphics Library (OpenGL) provides a function for applying an unprojection (in other words—registration) process directly on a two-dimensional data point(s).

With reference now to FIG. 1, the unprojection is done assuming iris 102 is a circular feature lying on plane $P_1$ that intersects the eyeball 100. Albeit mapped to an ellipse (as does cornea 103), the radius of the circular iris $$r_{iris} = \left(\frac{D_j}{2}\right),$$

is found in the calibration step (in centimeter scale). Eyeball (interchangeable with 'eye) 100 is initially modelled as a sphere having radius $r_e$. In the analysis, cornea 103 center is located along axis $X_L$, normal to iris 102 plane $P_1$ and which passes through the center $N_2$ of the ellipsoid feature that models iris 102. The distance $I_1$ of cornea 103 center $N_1$ from iris 103 center $N_2$ can be found in the calibration stage. Cornea 103 is modelled as an ellipsoid (see e.g., FIG. 1B) such that two of its axes ($D_{Major}$, $D_{Minor}$) lie on a plane $P_2$ parallel to iris 102 plane $P_1$. The radii $$r_{major} = \left(\frac{D_{Major}}{2}\right), r_{minor} = \left(\frac{D_{Minor}}{2}\right),$$

of the ellipsoid along these axes are chosen 309 such that the intersection of the iris plane with the ellipsoidal cornea results in a circular feature that is matches the iris contour. In other words, $$r_{minor} = r_{iris} = \left(\frac{D_j}{2}\right).$$

Next, pupil 104 is unprojected onto the same 3D coordinate system. The pupil is unprojected onto the ellipsoidal corneal surface $N_2$. Unprojected pupil 104 is then reverse-projected 310 onto iris 102 plane $P_1$ upon applying a refraction correction to estimate the pupil center. This is done by, for example, assuming an imaginary ray CP that originates at pupil 104 center, p=$N_2$, travels through the aqueous humour and cornea 103 (effective index of refraction≈1.3375) and refracts at a point of refraction $N_4$ on the surface of cornea 103 as it travels into the air (index of refraction≈1), such that the refracted ray passes through point $N_5$ of the optic sensor 151, and intersects image plane 152 of imaging module 150 at a point $N_6$. In an exemplary implementation, the location of the optical sensor is used as a fiducial, and the camera coordinate system is defined such that optical sensor 151 is located at its origin (e.g., $N_5$). Two of the axes of the camera coordinate system are parallel to the camera plane $P_C$ (see e.g., FIG. 1).

The line connecting the center of pupil 104 feature located 311 on iris 102 plane $P_1$ and the cornea 103 center $N_1$ is the optical axis $O_x$. In the context of the disclosure, the optical axis $O_x$, refers in an example to the vector connecting the pupil center on the iris plane with the cornea center. To this line ($O_x$), an angular rotation f(x) is applied about the cornea center to obtain 312 the visual line $V_x$(VL$_L$, VL$_R$) by:

$$V_x = R_h f(R_h^{-1} O_x)$$

Then the point of intersection 803$_j$(FIG. 8) of the visual lines (VL$_L$, VL$_R$) with the screen plane 802 is determined 314 and optionally display 315 the point of intersection 803$_j$ on screen 800 if such user interaction is required. Otherwise, the point of intersection 803$_j$ can be redefined as point of regard (PoR) of the user in 3D space.

To obtain the true visual axis for each eye, individual angular corrections need to be applied to each eye which will result in the visual axis, VL$_{L,R}$. The angular correction was obtained in an example, by:

$$VL = \begin{bmatrix} \hat{x} \\ \hat{y} \\ \hat{z} \end{bmatrix} + \begin{bmatrix} \cos(\phi+\alpha)\sin(y+\beta) \\ \sin(\phi+\alpha) \\ -\cos(\phi+\alpha)\sin(\phi+\beta) \end{bmatrix} t$$

Having the visual axis for both eyes (VL$_L$, VL$_R$), the PoR was defined as the intersection of these visual lines. However, due to small errors, VL$_L$, VL$_R$ did not intersect in 3D, the POR was therefore estimated as:

$$P\hat{O}R_i(\theta, E_L, E_R, \overline{IE}_L, \overline{IE}_R, r_I) = \mathrm{argmin}_{px,py,pz} d(VL_{LeftEye}, p)^2 + d(VL_{RightEye}, p)^2$$

s.t. PÔR in screen plane (See e.g., FIG. 3, 314)

Furthermore, parameters for Iris-Cornea offset, Cornea radius and cornea refraction index (denoted as: θ={IC, r$_C$, n$_{cornea}$, α, β}), were further optimized using the following Algorithm example, which yielded L calibration points, leading to the determination of these parameters by minimization of:

$$\hat{\theta}_L, \hat{\theta}_R = \mathrm{argmin}_{\theta_L, \theta_R} \sum_{(l=1)}^{L} \|P\hat{O}R_l(F_l, E_L, E_R, \overline{IE}_L, \overline{IE}_R, \theta_L, \theta_R, r_I) - POR_l\|_2^2$$

Figure 4:
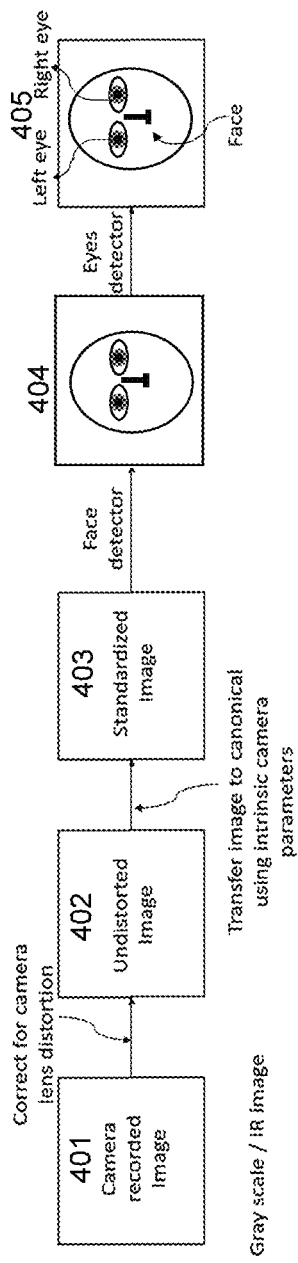
FIG. 4, is a schematic illustrating of the breakdown of image preprocessing routine.

Prior to determining convergence point 803$_j$ 804, Extrinsic calibration can be used to determine 313 the orientation between screen 800 plane 802 and imaging module 150 optic sensor 151. With reference to FIG. 4, it is noted that once an image is captured 401 from imaging module 150, distortion correction is applied to the image based on the known optical sensor 151 properties, 402—whereupon, the image is processed to obtain an 8-bit representation (grayscale) of the undistorted recorded image (using the intrinsic and distortion correction parameters disclosed hereinabove e.g., yielding standardized (canonical) image 403. The standardized image is then used as input to a face detector 404 and eye localizer 405 routines to locate the regions of the face and the eye in the image.

Figure 5:
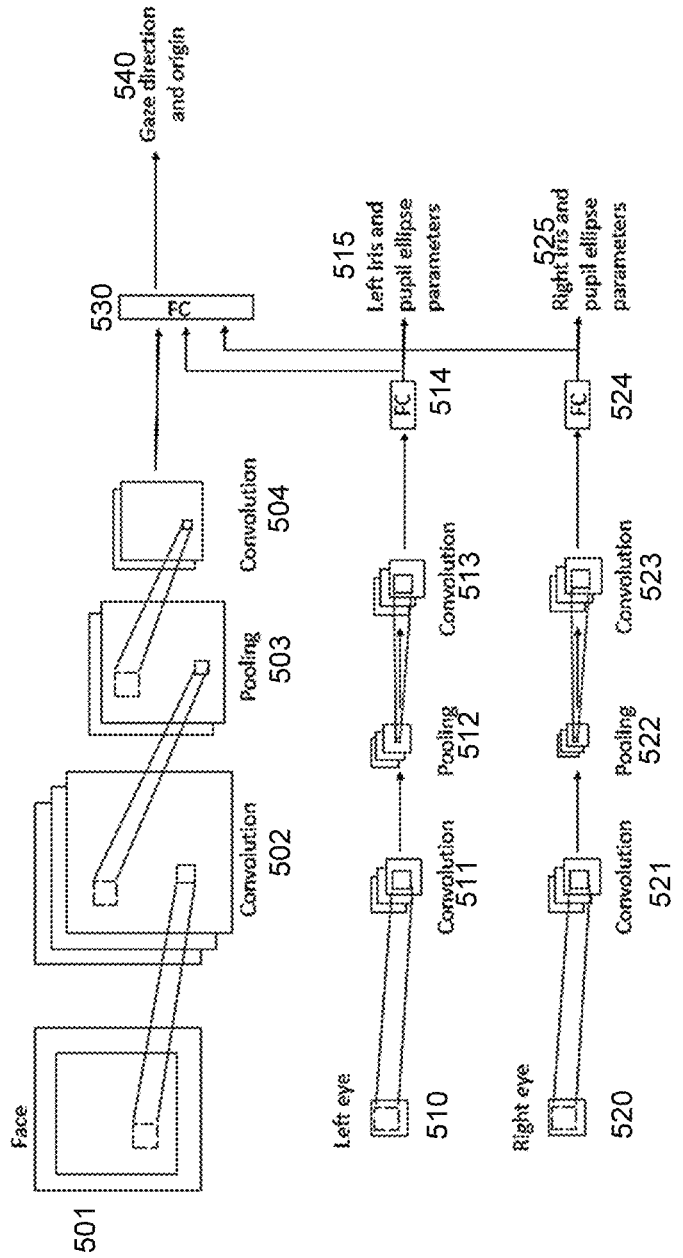
FIG. 5, illustrates an implementation of the deep neural network (DNN) used to learn the user's pattern in gazing.

Turning now to FIG. 5, corrected grayscale regions of the eyes (in other words, those isolated undistorted canonicals) are then fed 405 to a Deep Neural Network (DNN) that can be trained to locate pupil 104 and iris 102 ellipse contours on the image. Specifically, the output of the network can be five parameters that are used to describe an ellipse, namely, ellipse center $N_2$, radii (major and minor) of ellipse, and orientation. The unprojection of limbus contours of both eyes onto 3D space allow to compute the joint eye coordinate system and subsequently, the head pose of the user (FIGS. 1 and 2)

In an exemplary implementation, unprojection (or registration) of the pupil (see e.g., FIG. 3, 310) was carried out using the following algorithm:

At this stage, the remaining eye parameters were defined as population average values obtained from literature (see e.g., Beckerman et al., "*Variations in Eyeball Diameters of the Healthy Adults*", Journal of Ophthalmology Volume 2014, Article ID 503645, 5 pages http://dx.doi.org/10.1155/2014/503645). Rotation values were computed for each captured eye frame $F_i$ (obtained from the imaging module) given LP by obtaining iris plane coordinates with regard to the 6 DOF head pose, assuming fixed eyeball center, as well as the cornea center along an axis normal to the iris plane passing through the iris center:

$$\mathcal{R} = \mathrm{argmin}_R \left| \sum_{j=1}^{M} dist(LP_{i,j} - \wp(\mathcal{R}(EM))) \right|_2$$

Then, upon rotating the eye model, the M pupil landmarks were unprojected (registered) through the corneal surface, and onto the iris plane by an inverse ray-tracing.

For example, the 2D pupil landmarks points were denoted in pixels as PL$_m$, where m=1, . . . , M. The unprojection operation was carried out by first obtaining the 3D ray $\hat{e}_m$ along which the $PL_m=[x_{PL}, y_{PL}]_k^T$ landmark was located. To obtain $\hat{e}_m PL_m$ was multiplied by the inverse camera matrix to obtain $e_m$:

$$e_m = K^{-1}[x_{PL}, y_{PL}, 1]^T$$

And then normalized thus yielding $\hat{e}_m = e_m/|e_m|$

The $\hat{e}_m$ unit vector originated from the camera's origin and intersected the ellipsoidal corneal surface at $\rho_m$.

At $\rho_m$, the ray along $\hat{e}_m$ has undergone refraction, refracted ray, $\hat{e}_m^{ref}$ intersecting the iris plane and marking a location in 3D on the pupil boundary in the camera CS. $\hat{e}_m^{ref}$ was defined as:

$$\hat{e}_m^{ref} = \eta \hat{e}_m + (\eta <\hat{e}_m, \hat{n}> - \sqrt{1-\eta^2(1-<\hat{e}_m,\hat{n}>^2)})$$

Once all M (pupil landmarks) were unprojected onto the iris plane, their mean value was established as the pupil center (310).

Figure 9:
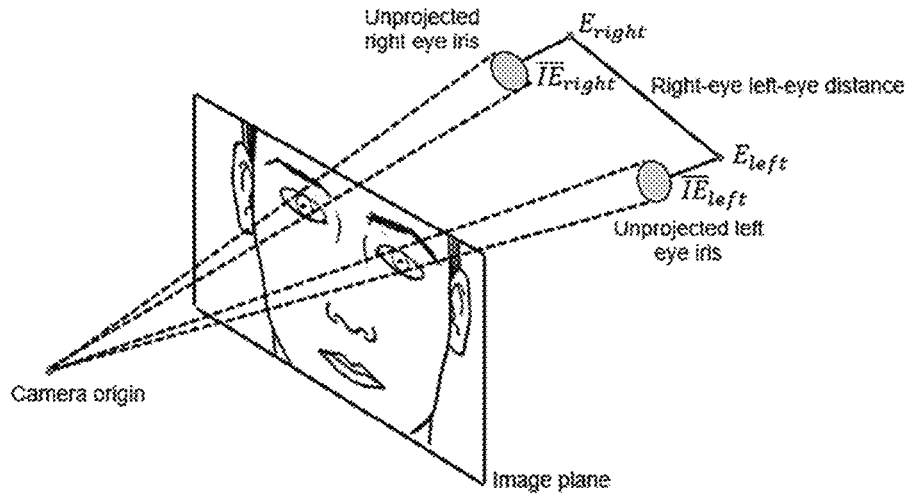
FIG. 9, illustrates the unprojection of iris contours of both eyes onto 3D space.
Figure 10:
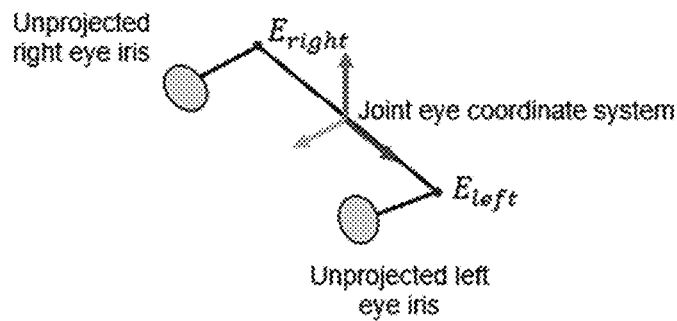
FIG. 10 is a detail of the unprojection of iris contours of both eyes onto 3D space illustrated in FIG. 9.

As illustrated schematically in FIG. 9, the positioning of the subject's head (in the 6 DOF head-pose constraint), are combined with extracted eye features (e.g., unprojected left and right eyes' Irises and the distance between them) input into neural network-connection for the final PoR determination, after a procedure of user-specific refinement over the initial targeted Gaze fixation (in other words the point of focus presented to the subject on the calibration screen). As illustrated in FIG. 9. Unprojection of iris contours of both eyes onto 3D space is illustrated in FIG. 10. As illustrated, the location of the 3D circular iris features, combined with visible facial features and non-visible features (e.g. eyeball center and corneal offset) allow to determine the head pose of the user, i.e. 6 DOF including head rotation (3 DOF) and position (3 DOF).

In an exemplary implementation, using DNN architecture of stacked hourglass is used because of the need to make the system user specific, implying the ability to capture data over a numerous (application-specific) scales and resolutions. Thus, the DNN can consist of, for example, at least three (3) Stacked Hourglass heat-maps, in three pipelines; one for the face 501 (a scale larger than the eyes landmark localizing), left eye 510, and right eye 520 modules (L and R eyes—same scale), with an input of eyes region image 510, 520, each of at least the size 100×100 pixels in another implementation. In the context of the disclosed methods, systems and programs provided, the term "stacked hourglass" refers in some implementations to the visualization of the initial sampling followed by the steps of pooling and subsequent convolution (or up-sampling) used to get the final output of the fully connected (FC) stack layers. Thus, the DNN architecture is configured to produce pixel-wise heat maps, whereby the hourglass network pools down to a very low resolution, then reconvolute and combines features across multiple resolutions.

For example, the hourglass for the right and left eyes can be set up as follows: Convolutional 511, 521, and max pooling 512, 522 layers are used to process features down to a very low resolution (of several pixels). At each max pooling step, 512, 522, the network branches off and applies more convolutions 513, 523 at the original pre-pooled resolution. After reaching the lowest resolution, the network begins the top-down sequence of up-sampling 514, 524 and combination of features across scales 515, 525. An image that, for any reason fails to fulfill this requirement (in other words, the ability to extract reliably the head pose in 6 DOF and the optical axis, can be rescaled to bring together information across two adjacent resolutions, by using nearest neighbor up-sampling of the lower resolution followed by an elementwise addition of the two (right and left eyes) sets of features (in other words, iris 102 ellipse and pupil 104 center parameters).

In an exemplary implementation, for each eyeball region that was successfully located by the detection algorithm, the DNN outputs the subject's iris and pupil elliptical contours, defined by the ellipse center, radii of ellipse, and their orientation. In addition, for each face image that was successfully located by the detection algorithm, the DNN outputs the subject's head location in 3D space (x, y, z, coordinates) in the camera coordinate system as well as the subject's roll, yaw, and pitch (see e.g., FIG. 2B). Additionally, another DNN receives as an input the face region 501 to train on estimating the gaze direction and origin. This DNN consists of a convolutional layer 502, followed by pooling 503, and another convolution layer 504 which is then used as input to a fully connected layer 530. The fully connected layer also obtains input from the eye-related DNN.

To improve the gaze prediction capability of the DNN for a specific subject, the DNN is continuously calibrated and trained on generated synthetic images that capture the geometrical structure of the subject eye, through his estimated intrinsic parameters as well as real-data collected from the subject at the time of calibration.

The full facial analysis, as part of the gaze prediction, is carried out since the facial features extracted by the systems and algorithms disclosed herein, are inherently related to the shape of the subject's skull and facial muscle movement. The face analysis is used in an exemplary implementation, to compensate for the eyeball's relocation and gaze direction change with respect to a base facial posture due to facial expressions. For example, when the user is raising his/hers eyebrows, or squints, the location of the eyeball with respect to facial landmarks may change.

Moreover, should a calibration procedure be required, the DNN can be used to detect pupil and iris (in other words, the Limbus) contours (e.g., user specific mapped iris ellipse radii and plane $P_1$, $P_2$ distances $L_I$, as well as other intrinsic parameters (for example, Iris-Cornea offset, Cornea radius and cornea refraction index) and used as input to the algorithm (initial hourglass stack) described herein to obtain general gaze direction of the user. The personal calibration is done to allow a more accurate user-specific gaze inference. The eye parameters of human subjects vary from person to person as well as from left to right eye. For example, the subject's iris radius varies from person to person, and it is this variable that allows determining the location of the eye in the (3D) coordinates system.

For the iris-based calibration the eyeball center can be initially estimated based on multiple frames with limbus points (LP) localized. At this stage, four variables are determined: x, y, z of eyeball center, and iris-center-eyeball-center offset:

$$\hat{x}, \hat{y}, \hat{z} \overline{offset} = \mathrm{argmin}_{x,y,z,offset} \Sigma_{i=1}^N |\Sigma_{j=1}^M \mathrm{dist} (LP_{i,j} - \wp(\mathcal{R}_i(EM)))|_2 \quad \text{EQU. 1}$$

where, EM is the eye model, $\mathcal{R}$(EM) is the rotation matrix applied to the eye model, and $\wp(\cdot)$ is the projection of the 3D iris onto the image plane.

TABLE 1

Eye model parameters used in the invention.

| Symbol | Meaning | Obtained By |
| --- | --- | --- |
| E | Eyeball center (x, y, z) | Iris-based optimization |
| $\overline{IC}$ | Iris-Cornea offset | Gaze-based optimization |
| $\overline{IE}$ | Iris-Eye-center offset | Iris-based optimization |
| $r_i$ | Iris radius | Gaze-based optimization |
| $r_c$ | Cornea major axis radius | Gaze-based optimization |
| α, β | Angular corrections to visual axis | Gaze-based optimization |

Figure 11:
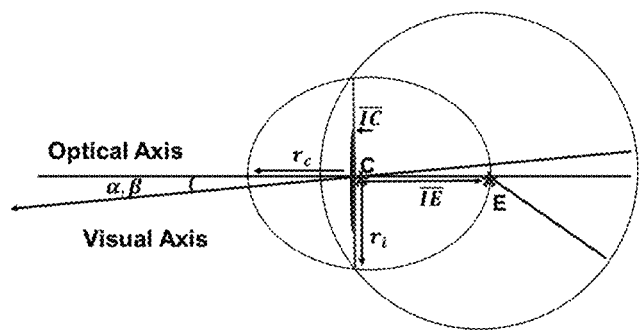
FIG. 11, is an implementation of an eye model used in the systems and methods described.

Then, given ground-truth location of subject's point of interest $801_i$ that is collected in the calibration stage, the optimal intrinsic eye parameters (noted in Table 1 and shown in FIG. 11) are established, which can then be used to improve accuracy of the gaze-predicting algorithm. If the calibration stage cannot be performed, average eye parameters' values of subjects' population can be used in another implementation in the initial algorithm.

The gaze direction is used an input to the final regression layers of the face-based DNN as shown in FIG. 10 to provide a refined estimate of the gaze direction and origin. This Gaze correction is user specific, and obtained through data collection and augmentation, this enables it to be free of any model underpinning, as it is based on minimization of a specific subject's Gaze error for whom it was trained.

The systems, methods and programs for providing a point of reference (PoR) in a 3D field and/or 2D plane, can be used for example, in mixed or layered reality applications that is personalized to the specific user using, inter-alia: using machine learning methods that include at least one of the following: procedure using mixed data for training ("real"—user collected and "synthetic"—computer generated data); development of a machine-learning (Deep Learning) architecture inspired by the geometrical and physiological properties of the human eye; optimization of the machine-learning framework that will enable a real-time performance (e.g., NLT 30 frames per second (fps)), on a limited computing power device (e.g., Mobile-phone, Exynos, VPU-MOVIDIUS™ and the like etc.).

It is noted, that machine learning is used in an exemplary implementation to provide a user-specific parameters. To achieve this, the training set used can comprise images captured during the calibration steps described herein. For the training procedure, synthetic (e.g., external databases) as well as real facial images of the user having eye-regions as shown in FIG. 1B of size 200×200 pixels along with their corresponding PoR ($803_j$) are used to train the DML. In addition, a smaller sized eye region with minimal size of 100×100 pixels can be used, that is up-scaled to size of 200×200 pixels through non-linear extrapolation. The training data includes in certain implementations, users' of varying ethnicity, geographical location that were recorded in outdoor and indoor lighting conditions from various distances. Likewise, validation set can be comprised of the same type of image data used for the training; however, the images in the validation dataset were not present in the training data. The data in the validation set includes recorded images of the same user but at different recording sessions (and again, at different lighting and distances, on other words—scale, resolution and focal points). Moreover, the test set is comprised of the same type of data used for the training; however, the images in the test dataset were not present in neither the training nor the validation dataset. The data in the test set did include recorded images of the same user as in the training and validation set but at different recording sessions as described above in reference to lighting and distances inter-alia.

In an example, the dataset was captured in a system which comprised four IR and four RGB-D based optical sensors (which capture RGB images along their with per-pixel depth information), located at the corners of screen 800 (see e.g., FIG. 8), with which the subject interacts. In addition, the system had two LED lights. In another implementation, the aforementioned components are further included in the systems described herein for providing real-time 6 DOF posture-constrained PoR.

Furthermore, the Gaze estimation (interchangeable with point of reference (PoR), or point of regard) system is of high-precision (less than 1 degrees of accuracy referring to the angular location of the eye relative to the optic sensor array). The Gaze estimation systems, methods and programs for providing a point of reference in a 3D space and/or 2D plane, based on constrained oculometry, will further comprise the prediction of Gaze direction to support foveal rendering capabilities (in other words, a process, in which the region of an image that is the focus of the eye falling upon the fovea, is rendered with a higher resolution, while the remainder of the image is rendered at a lower resolution). Likewise, the systems, methods and programs for providing a point of reference (PoR) in a 3D field and/or 2D plane, based on personalized, constrained oculometry will further comprise the capabilities of on-line, real-time calibration, and the estimation of the subject's internal parameters (e.g., pupillary distance (IPD), Pupil-size boundaries, Eye-ball center and radius, visual-axis deviation etc.).

Examples of applications are illustrated schematically in FIGS. 6A, and 6B. As illustrated in FIG. 6A, user faced optic sensor (151, FIG. 1) capture the user image 601, following optionally the rendering of a point of reference on the mobile device screen (see e.g., 802, FIG. 8), the image is preprocessed 602, whereupon gaze direction and origin are analyzed and compared against the user-specific distance between, for example a dataset of the subject's distance between Limbus 102 plane $P_1$ and cornea 103 center plane $P_2$, as well as the specific corneal curvature defined by $r_c$. Once a predetermined correlation threshold is acquired, authorizing the user will be enabled 604 and the device is unlocked 605.

In example illustrated in FIG. 6B, time of focus can be assessed, where various screen objects are rendered on the display, each rendering followed by capturing image 610, followed by preprocessing of the captured image 611, whereupon gaze direction and origin are analyzed 612 and the PoR is compared against the screen objects rendered 613 leading to assessment of focus time 614. In addition, the disclosure can classify whether the user is blinking, sleeping, or averts his or her gaze from a predefined gaze direction.

It is noted that the term "imaging module" as used herein means a unit that includes a plurality of built-in image and/or optic sensors and outputs electrical signals, which have been obtained through photoelectric conversion, as an image, while the term "module" refers to software, hardware, for example, a processor, or a combination thereof that is programmed with instructions for carrying an algorithm or method. The modules described herein may communicate through a wired connection, for example, a hard-wired connections, a local area network, or the modules may communicate wirelessly. The imaging module may comprise charge coupled devices (CCDs), a complimentary metal-oxide semiconductor (CMOS) or a combination comprising one or more of the foregoing. If static images are required, the imaging module can comprise a digital frame camera, where the field of view (FOV) can be predetermined by, for example, the camera size and the distance from the subject's face. The cameras used in the imaging modules of the systems and methods disclosed, can be a digital camera. The term "digital camera" refers in certain implementations to a digital still camera, a digital video recorder that can capture a still image of an object and the like. The digital camera can comprise an image capturing unit or module, a capture controlling module, a processing unit (which can be the same or separate from the central processing module).

Capturing the image can be done with, for example image capturing means such as a CCD solid image capturing device of the full-frame transfer type, and/or a CMOS-type solid image capturing device, or their combination.

The systems used herein can be computerized systems further comprising a central processing module; a display module; and a user interface module. The Display modules, which can include display elements, which may include any type of element which acts as a display. A typical example is a Liquid Crystal Display (LCD). LCD for example, includes a transparent electrode plate arranged on each side of a liquid crystal. There are however, many other forms of displays, for example OLED displays and Bi-stable displays. New display technologies are also being developed constantly. Therefore, the term display should be interpreted widely and should not be associated with a single display technology. Also, the display module may be mounted on a printed circuit board (PCB) of an electronic device, arranged within a protective housing and the display module is protected from damage by a glass or plastic plate arranged over the display element and attached to the housing.

Additionally, "user interface module" broadly refers to any visual, graphical, tactile, audible, sensory, or other means of providing information to and/or receiving information from a user or other entity. For example, a set of instructions which enable presenting a graphical user interface (GUI) on a display module to a user for displaying and changing and or inputting data associated with a data object in data fields. In an exemplary implementation, the user interface module is capable of displaying any data that it reads from the imaging module.

As indicated, the systems implementing the methods provided, using the programs provided can further comprise a central processing module; a display module; and a user interface module. The term 'module', as used herein, means, but is not limited to, a software or hardware component, such as a Field Programmable Gate-Array (FPGA) or Application-Specific Integrated Circuit (ASIC), which performs certain tasks. A module may advantageously be configured to reside on an addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

In an implementation, the systems provided herein are implementing the methods described. Accordingly, provided herein is a method of providing at least one of a user specific: eye location, gaze direction, and PoR, implementable in a system comprising an imaging module comprising an optic sensor directed to the user, a display, a graphic processing module (GPM), a central processing module (CPM), wherein the CPM is in communication with the imaging module, the display, the GPM and a memory having thereon a processor-readable media with set of executable instructions, the method comprising: using the imaging module, capturing an image of the subject's face; extracting a plurality of features from the captured image; using the plurality of extracted features, establishing the subject's head pose in a predetermined Cartesian coordinate system; unprojecting the subject's pupil and Iris of both eyes from a portion of the plurality of extracted features, into the predetermined Cartesian coordinate system, forming a right eye and a left eye unprojected, three dimensional (3D) contours; and using the right and left eyes' unprojected, three dimensional (3D) contours, determining at least one of eye location, gaze direction, and point of regard (PoR).

Figure 7A:
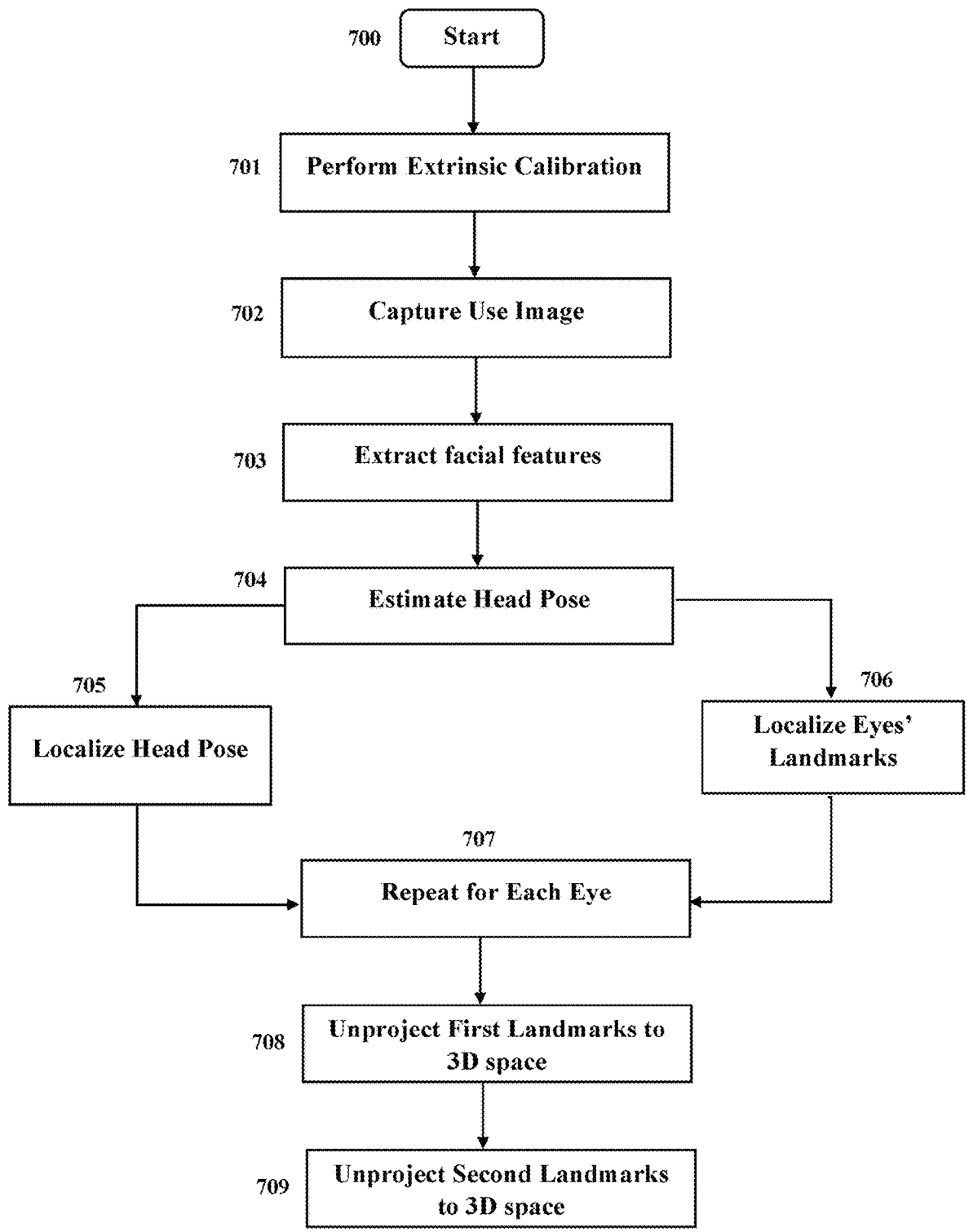
FIGS. 7A-7B, illustrate a flow chart of an implementation for implementing the method of determining PoR using the systems and programs disclosed.
Figure 7B:
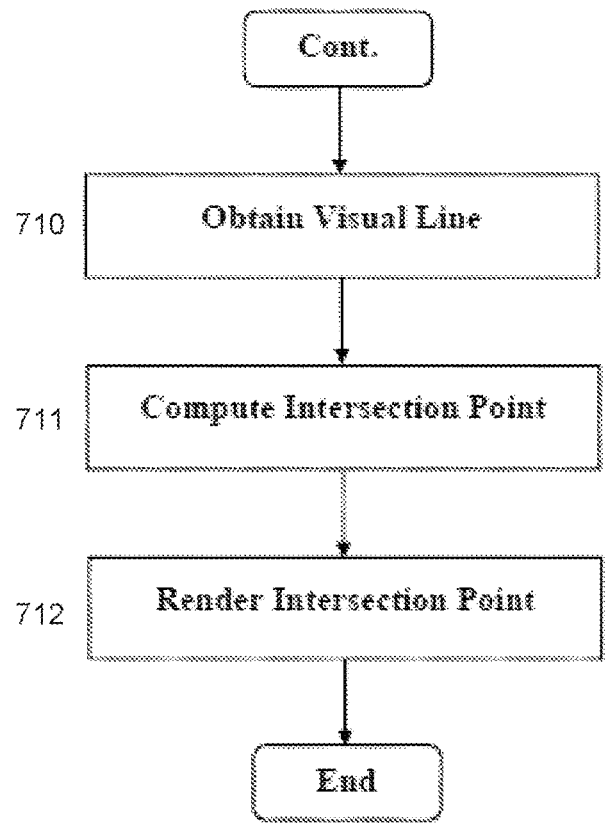

A schematic illustration of the methods described herein is illustrated in FIGS. 7A-7B. As illustrated, following extrinsic calibration 701, user image is captured 702, whereupon facial features are extracted 703, and head pose is estimated 704. In parallel the head pose is set in 6 DOF 705 and the left and right eyes landmarks (e.g., iris ellipse parameters and pupil center) are localized 706 for both eyes 707. Then the first set (e.g., left eye parameters constrained by 6 DOF head pose) of landmarks is unprojected 708 to the 3D space, followed by the second set (e.g., right eye parameters constrained by 6 DOF head pose) of landmarks 709, whereupon visual lines (VLL, VLR) are obtained 710 and their intersection point (see e.g., $803_j$, FIG. 8) is computed 711. Once computed, the intersection point can be rendered 712 or the PoR identified in the 3D space.

In the context of the various implementations, examples and embodiments disclosed herein, the term "render" does not make any assumptions as to whether the rendering process is performed by software rendering or by hardware rendering, but rather to produce a 2D graphics image on an output (e.g., display) device from a 3D coordinates' data file.

Unless specifically stated otherwise, as apparent from the discussions, it is appreciated that throughout the specification discussions utilizing terms such as "processing," "loading," "in communication," "detecting," "calculating," "determining", "analyzing," or the like, refer to the action and/or processes of a computer or computing system, or similar electronic computing device, that manipulate and/or transform data represented as physical, such as the PoR into other data similarly represented as physical layers, such as the transformed data.

As indicated, provided herein is a computer program, comprising program code means for carrying out the steps of the methods described herein, as well as a computer program product (e.g., a micro-controller) comprising program code means stored on a medium that can be read by a computer, such as a hard disk, CD-ROM, DVD, USB memory stick, or a storage medium that can be accessed via a data network, such as the Internet or Intranet, when the computer program product is loaded in the main memory of a computer [or micro-controller] and is carried out by the computer [or micro controller].

Furthermore, provided herein is a computer-readable medium comprising the executable instructions disclosed. Accordingly, provided herein is a processor readable media for providing at least one of a user specific: eye location, gaze direction, and PoR, implementable in a system comprising an imaging module with an optic sensor directed to a user, a display, a graphic processing module (GPM), and a central processing module (CPM), wherein the CPM is in communication with the imaging module, the display, the GPM and a memory having thereon the processor-readable media, comprising a set of executable instructions configured when executed, to cause the CPM to: using the imaging module, capture an image of the subject's face; extract a plurality of features from the captured image; using the plurality of extracted features, establishing the subject's head pose in a predetermined Cartesian coordinate system; unproject the subject's pupil and Iris of both eyes from a portion of the plurality of extracted features, into the predetermined Cartesian coordinate system, forming a right eye and a left eye unprojected, three dimensional (3D) contours; and using the right and left eyes' unprojected, three dimensional (3D) contours, determine at least one of eye location, gaze direction, and point of regard (PoR).

In the context if the disclosure and the various implementations, the term "graphic processing module" (GPM) refers to a programmable logic chip (processor) specialized for display functions. The GPM renders images, animations and video for the display, the GPM can further comprise specialized firmware for performing the various functions, steps and operations disclosed herein. Moreover, the term "module" or "component" may refer in certain exemplary implementations to software objects or routines that execute on computing systems. The different components, modules, engines, and steps described herein may be implemented as objects or processes that execute on the computing system (e.g., as separate threads). While the system and methods described herein are preferably implemented in software, implementations in hardware or a combination of software and hardware are also possible and contemplated.

The term "computer-readable medium" as used herein, in addition to having its ordinary meaning, refers to any medium that participates in providing instructions to at least one processor for execution. Such a medium may take many forms, including but not limited to, non-volatile media and volatile media. Non-volatile media can be, for example, optical or magnetic disks, such as a storage device. Volatile media includes dynamic memory, such as main memory.

Memory device as used in the methods, programs and systems described herein can be any of various types of memory devices or storage devices. The term "memory device" is intended to encompass an installation medium, e.g., a CD-ROM, floppy disks, or tape device; a computer system memory or random access memory such as DRAM, DDR RAM, SRAM, EDO RAM, Rambus RAM, etc.; or a non-volatile memory such as a magnetic media, e.g., a hard drive, optical storage, or ROM, EPROM, FLASH, etc. The memory device may comprise other types of memory as well, or combinations thereof. In addition, the memory medium may be located in a first computer in which the programs are executed (e.g., a training computer), and/or may be located in a second different computer [or micro controller] which connects to the first computer over a network, such as the Internet [remark: they might be even not connected and information will be transferred using USB stick]. In the latter instance, the second computer may further provide program instructions to the first computer for execution. The term "memory device" can also include two or more memory devices which may reside in different locations, e.g., in different computers that are connected over a network.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the stack(s) includes one or more stack). Reference throughout the specification to "one implementation", "another implementation", "an implementation", and so forth, when present, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

Accordingly, provided herein is a system for providing a user specific gaze estimation, the system comprising: an imaging module comprising an optic sensor directed to the subject; a display; a graphic processing module (GPM); a central processing module (CPM) comprising at least one processor, in communication with the imaging module, the display, the GPM and a memory having thereon a processor-readable media with set of executable instructions configured, when executed to cause the at least one processor to: using the imaging module, capture an image of the subject's face; extract a plurality of features from the captured image; using the plurality of extracted features, determine the subject's head pose in a predetermined Cartesian coordinate system; unproject the subject's pupil and Limbus of both eyeballs from a portion of the plurality of extracted features, into the predetermined Cartesian coordinate system, forming a right eyeball and a left eyeball unprojected, three dimensional (3D) contours; and using each of the right and left eyeballs' unprojected, three dimensional (3D) contours, determine at least one of eye location, gaze direction, and point of regard (PoR), wherein the eyeball center is fixed in the Cartesian coordinates, thus providing anatomical constraints, wherein (i) the set of executable instructions, when executed and before capturing the image of the user face, are configured to cause the at least one processor to perform a calibration configured to provide the user-specific eyeball movement, (ii) the calibration comprises determining at least one of: the relative position and orientation of the display with respect to the optic sensor and the intrinsic parameters of the sensor, wherein (iii) the set of executable instructions, when executed, is configured to cause the at least one processor to: using the GPM, render a point of reference on the display; and using the optic sensor, capture a plurality of images of the subject's interaction with point of reference on the display, wherein (iv) the set of executable instructions, when executed, is configured to cause the at least one processor to: apply distortion correction to the at least one image captured, forming at least one undistorted image; perform face detection and a left- and a right eyeball localization on the at least one undistorted image. using the CPM, apply a first convoluted neural network (CNN) algorithm to detect, analyze, and localize the subject's head pose in six (6) degrees of freedom (DoF) to the predetermined Cartesian coordinate system from the undistorted image, thus providing a reference head orientation ($R_h$); using the CPM, apply a second CNN algorithm to localize the left- and right eyeballs' pupil and Iris on the localized eyeball region, (v) each of the left, and right eyeballs' region comprises a quadrilateral polygon of at least 100 pixel by 100 pixel extending between the corners of each eyeball as well as between the upper and lower eyelids, when the eyelid of each eyeball is open, (vi) the set of executable instructions, when executed and before performing face detection and a left- and a right eyeball localization on the at least one undistorted image, are further configured to cause the at least one processor to render a standardized, 8 bit gray scale image, and wherein (vii) the head pose is mapped relative to the camera in the predetermined Cartesian coordinate system, providing at least one of 3D coordinate, angular orientation, and estimation of the non-visible internal eyeball features (e.g., eyeball center).

In another exemplary implementation, provided herein is a method of providing at least one of a user specific: eyeball location, gaze direction, and PoR, implementable in a system comprising an imaging module comprising an optic sensor directed to the user, a display, a graphic processing module (GPM), a central processing module (CPM), wherein the CPM is in communication with the imaging module, the display, the GPM and a memory having thereon a processor-readable media with set of executable instructions, the method comprising: using the imaging module, capturing an image of the subject's face; extracting a plurality of features from the captured image; using the plurality of extracted features, establishing the subject's head pose in a predetermined Cartesian coordinate system; unprojecting the subject's pupil and Iris of both eyeballs from a portion of the plurality of extracted features, into the predetermined Cartesian coordinate system, forming a right eyeball and a left eyeball unprojected, three dimensional (3D) contours; and using the right and left eyeballs' unprojected, three dimensional (3D) contours, determining at least one of eyeball location, gaze direction, and point of regard (PoR), wherein the eyeball center is fixed in the Cartesian coordinates, thus providing anatomical constraints, further comprising (viii) before the step of capturing, performing a calibration configured to provide the user-specific eyeball movement pattern, (ix) the calibration comprises determining the relative position and orientation of the display with respect to the optic sensor (in other words, a component of the imaging module), further comprising (x) using the GPM, rendering a point of reference on the display; using the optic sensor, capturing at least one image of the subject's interaction with point of reference on the display; applying distortion correction to the at least one image captured, forming at least one undistorted image; performing face detection and a left- and a right eyeball localizing on the at least one undistorted image. using the CPM, applying a first convoluted neural network (CNN) algorithm to detect, analyze, and localize the subject's head pose in six (6) degrees of freedom (DoF) to the predetermined Cartesian coordinate system from the undistorted image, thus providing a reference head orientation ($R_h$); using the CPM, applying a second CNN algorithm to localize the left- and right eyeballs' pupil and Iris on the localized eyeball region, (xi) each of the left, and right eyeballs' region comprises a quadrilateral polygon of at least 100 pixel by 100 pixel extending between the corners of each eyeball as well as between the upper and lower eyelids, when the eyeball is open, (xii) before the step of performing face detection and a left- and a right eyeball localization, further using the GPM, rendering a standardized, 8 bit gray scale image, and wherein (xiii) the head pose is mapped relative to the camera in the predetermined Cartesian coordinate system, providing 3D coordinate, and angular orientation.

In yet another implementation, provided herein is a processor-readable media for providing at least one of a user specific: eyeball location, gaze direction, and PoR, implementable in a system comprising an imaging module with an optic sensor directed to a user, a display, a graphic processing module (GPM), and a central processing module (CPM), wherein the CPM comprises at least one processor, and is in communication with the imaging module, the display, the GPM and a memory having thereon the processor-readable media, comprising a set of executable instructions configured when executed, to cause the at least one processor to: using the imaging module, capture an image of the subject's face; extract a plurality of features from the captured image; using the plurality of extracted features, establishing the subject's head pose in a predetermined Cartesian coordinate system; unproject the subject's pupil and Iris of both eyeballs from a portion of the plurality of extracted features, into the predetermined Cartesian coordinate system, forming a right eyeball and a left eyeball unprojected, three dimensional (3D) contours; and using the right and left eyeballs' unprojected, three dimensional (3D) contours, determine at least one of eyeball location, gaze direction, and point of regard (PoR), wherein the eyeball center is fixed in the Cartesian coordinates, thus providing anatomical constraints, wherein (xiv) the set of executable instructions are further configured when executed, to cause the at least one processor to perform a calibration configured to provide the user-specific eyeball movement pattern, (xv) the calibration comprises determining the relative position and orientation of the display with respect to the optic sensor, wherein (xvi) the set of executable instructions are further configured when executed, to cause the at least one processor to: using the GPM, render a point of reference on the display; and using the optic sensor, capturing at least one image of the subject's interaction with point of reference on the display, and wherein (xvii) wherein the set of executable instructions are configured when executed, to cause the at least one processor to: apply distortion correction to the at least one image captured, forming at least one undistorted image; perform face detection and a left- and a right eyeball localizing on the at least one undistorted image. using the CPM, apply a first convoluted neural network (CNN) algorithm to detect, analyze, and localize the subject's head pose in six (6) degrees of freedom (DoF) to the predetermined Cartesian coordinate system from the undistorted image, thus providing a reference head orientation ($R_h$); and using the CPM, apply a second CNN algorithm to localize the left- and right eyeballs' pupil and Iris on the localized eyeball region Although the foregoing disclosure for systems, methods and programs for providing a point of reference (PoR) in a 3D field and/or 2D plane, based on anatomically constrained oculometry has been described in terms of some implementations, other embodiments, implementations, and examples will be apparent to those of ordinary skill in the art from the disclosure herein. Moreover, the described embodiments have been presented by way of example only, and are not intended to limit the scope of the embodiments. Indeed, the novel methods, programs, and systems described herein may be embodied in a variety of other forms without departing from the spirit thereof. Accordingly, other combinations, omissions, substitutions and modifications will be apparent to the skilled artisan in view of the disclosure herein.

While the invention has been described in detail and with reference to specific embodiments thereof, it will be apparent to one of ordinary skill in the art that various changes and modifications can be made therein without departing from the spirit and scope thereof. Accordingly, it is intended that the present disclosure covers the modifications and variations of this invention provided they come within the scope of the appended claims and their equivalents.

What is claimed is:

1. A system for providing user-specific gaze estimation, the system comprising:
   a. circuitry configured to perform a calibration for a subject, the calibration including at least determining at least one of:
      a) a relative position and orientation of a display with respect to an optical sensor; or
      b) at least one intrinsic parameter of the optical sensor;
   b. circuitry configured to capture an image of the subject's face, wherein distortion correction is applied to at least one captured image of the subject's face;
   c. circuitry configured to perform left and right eyeball localization on at least one distortion-corrected captured image of the subject's face;
   d. circuitry configured to extract a plurality of features from the at least one distortion-corrected captured image;
   e. circuitry configured to determine the subject's head pose in a predetermined Cartesian coordinate system based at least in part on the plurality of extracted features;
   f. circuitry configured to unproject the subject's irises from a portion of the plurality of extracted features into the predetermined Cartesian coordinate system, forming right and left unprojected three-dimensional (3D) iris contours; and
   g. circuitry configured to use each of the right and left eyeballs' unprojected three-dimensional (3D) iris contours to determine at least one of eye location, gaze direction, or point of regard (PoR), wherein an eyeball center is fixed in the predetermined Cartesian coordinate system, thus providing anatomical constraints.

2. The system of claim 1, wherein the circuitry configured to perform a calibration for a subject comprises circuitry configured to:
   a) render a point of reference on the display; and
   b) capture a plurality of images of the subject's interaction with the at least one point of reference on the display.

3. The system of claim 1, wherein the circuitry configured to determine the subject's head pose in a predetermined Cartesian coordinate system based at least in part on the plurality of extracted features comprises circuitry configured to apply a first convolutional neural network (CNN) algorithm to detect and localize the subject's head pose in six (6) degrees of freedom (DoF) to the predetermined Cartesian coordinate system, thus providing a reference head orientation (Rh).

4. The system of claim 3, wherein the circuitry configured to apply a first convolutional neural network (CNN) algorithm further comprises circuitry configured to apply a second CNN algorithm to localize the left and right eyeballs' irises to a localized eyeball region b.

5. The system of claim 4, wherein each of the left and right eyeballs' localized eyeball region comprises a quadrilateral polygon of at least 100 pixels by 100 pixels extending between the corners of each eyeball as well as between the upper and lower eyelids, when the eyelid of each eyeball is open.

6. The system of claim 5, wherein the circuitry configured to perform left and right eyeball localization on at least one distortion-corrected captured image of the subject's face is further configured to render a standardized image prior to performing the left and right eyeball localization on at least one distortion-corrected captured image.

7. The system of claim 1, wherein the circuitry configured to determine the subject's head pose in a predetermined Cartesian coordinate system based at least in part on the plurality of extracted features comprises circuitry configured to map head pose relative to the optical sensor in the predetermined Cartesian coordinate system, providing at least one of 3D coordinates, angular orientation, or estimation of one or more non-visible internal eyeball features.

8. A computer-implemented method of providing at least one of a user specific: eyeball location, gaze direction, or PoR, the method comprising:
   a. performing a calibration for a subject, the calibration including at least determining at least one of:
      a) a relative position and orientation of a display with respect to an optical sensor; or
      b) at least one intrinsic parameter of the optical sensor;
   b. capturing a digital image of the subject's face, wherein distortion correction is applied to at least one captured digital image of the subject's face;
   c. performing left and right eyeball localization on at least one distortion-corrected captured image of the subject's face;
   d. extracting a plurality of features from the at least one distortion-corrected captured image;
   e. determining the subject's head pose in a predetermined Cartesian coordinate system based at least in part on the plurality of extracted features;
   f. unprojecting the subject's irises from a portion of the plurality of extracted features into the predetermined Cartesian coordinate system, forming right and left unprojected three-dimensional (3D) iris contours; and
   g. using each of the right and left eyeballs' unprojected three-dimensional three dimensional (3D) iris contours to determine at least one of eye location, gaze direction, or point of regard (PoR), wherein an eyeball center is fixed in the predetermined Cartesian coordinate system, thus providing anatomical constraints.

9. The method of claim 8, wherein each of the left and right eyeballs' localized eyeball region comprises a quadrilateral polygon of at least 100 pixels by 100 pixels extending between the corners of each eyeball as well as between the upper and lower eyelids, when the eyeball is open.

10. The method of claim 9, further comprising rendering a standardized image prior to performing the left and right eyeball localization on at least one distortion-corrected captured image of the subject's face.

11. The method of claim 8, wherein the head pose is mapped relative to the optical sensor in the predetermined Cartesian coordinate system, providing 3D coordinates and angular orientation.

12. The method of claim 8, wherein the performing a calibration for a subject comprises:
   a) rendering a point of reference on the display; and
   b) capturing a plurality of images of the subject's interaction with the at least one point of reference on the display.

13. The method of claim 8, wherein the determining the subject's head pose in a predetermined Cartesian coordinate system based at least in part on the plurality of extracted features comprises mapping head pose relative to the optical sensor in the predetermined Cartesian coordinate system to provide at least one of 3D coordinates, angular orientation, or estimation of one or more non-visible internal eyeball features.

14. A non-transitory processor-readable medium for providing at least one of a user specific: eyeball location, gaze direction, or PoR, the medium including a set of executable instructions configured, when executed, to cause at least one processor to:
  a. perform a calibration for a subject, the calibration including at least determining at least one of:
    a) a relative position and orientation of a display with respect to an optical sensor; or
    b) at least one intrinsic parameter of the optical sensor;
  b. capture a digital image of the subject's face, wherein distortion correction is applied to at least one captured digital image of the subject's face;
  c. perform left and right eyeball localization on at least one distortion-corrected captured image of the subject's face;
  d. extract a plurality of features from the at least one distortion-corrected captured image;
  e. determine the subject's head pose in a predetermined Cartesian coordinate system based at least in part on the plurality of extracted features;
  f. unproject the subject's irises from a portion of the plurality of extracted features into the predetermined Cartesian coordinate system, forming right and left unprojected three-dimensional (3D) iris contours; and
  g. use each of the right and left eyeballs' unprojected three-dimensional (3D) iris contours to determine at least one of eye location, gaze direction, or point of regard (PoR), wherein an eyeball center is fixed in the predetermined Cartesian coordinate system, thus providing anatomical constraints.

15. The non-transitory processor-readable medium of claim 14, wherein the set of executable instructions is further configured, when executed, to cause the at least one processor to perform a calibration configured to provide a user-specific eyeball movement pattern.

16. The non-transitory processor-readable medium of claim 14, wherein the user-specific eyeball movement pattern comprises a pattern of dwells and saccades.

17. The non-transitory processor-readable medium of claim 14, wherein the set of executable instructions is further configured, when executed, to cause the at least one processor to:
  a. render a point of reference on the display; and
  b. using the optic sensor, capture at least one image of the subject's interaction with the point of reference on the display.

18. The non-transitory processor-readable medium of claim 14, wherein the set of executable instructions is configured, when executed, to cause the at least one processor to:
  a. perform face detection and a left and a right eyeball localization on the at least one distortion-corrected image;
  b. apply the first convoluted neural network (CNN) algorithm to detect, analyze, and localize the subject's head pose in six (6) degrees of freedom (DoF) to the predetermined Cartesian coordinate system from the distortion-corrected image, thus providing a reference head orientation (Rh); and
  c. apply the second CNN algorithm to localize the left and right eyeballs' pupil and iris on the localized eyeball region.

19. The non-transitory processor-readable medium of claim 14, wherein the perform a calibration for a subject instruction comprises instructions to:
  a. render a point of reference on the display; and
  b. capture a plurality of images of the subject's interaction with the at least one point of reference on the display.

20. The non-transitory processor-readable medium of claim 14, wherein the determine the subject's head pose in a predetermined Cartesian coordinate system based at least in part on the plurality of extracted features instruction comprises instructions to map head pose relative to the optical sensor in the predetermined Cartesian coordinate system to provide at least one of 3D coordinates, angular orientation, or estimation of one or more non-visible internal eyeball features.

* * * * *